United States Patent [19]

Klose et al.

[11] 4,019,961

[45] Apr. 26, 1977

[54] ANALYTICAL ENZYMATIC DETERMINATION

[75] Inventors: Sigmar Klose; August Wilhelm Wahlefeld, both of Weilheim; Alexander Hagen, Tutzing, all of Germany

[73] Assignee: Boehringer Mannheim G.m.b.H., Mannheim-Waldhof, Germany

[22] Filed: Mar. 10, 1975

[21] Appl. No.: 556,961

[30] Foreign Application Priority Data

Mar. 14, 1974 Germany ............................ 2412354

[52] U.S. Cl. ....................................... 195/103.5 R
[51] Int. Cl.$^2$ ........................................ G01N 31/14
[58] Field of Search ...................... 195/103.5 R, 127

[56] References Cited

UNITED STATES PATENTS

| | | | |
|---|---|---|---|
| 3,526,480 | 9/1970 | Findl et al. | 195/103.5 R |
| 3,703,591 | 11/1972 | Bucolo et al. | 195/103.5 R |
| 3,862,009 | 1/1975 | Wahlefeld et al. | 195/103.5 R |

OTHER PUBLICATIONS

R. Bonnichsen, "Ethanol" H. U. Bergmeyer, Methods of Enzymatic Analysis, Academic Press, N.Y. and London, pp. 285–287, (1965).

*Primary Examiner*—Lionel M. Shapiro
*Assistant Examiner*—C. A. Fan
*Attorney, Agent, or Firm*—Weiser, Stapler & Spivak

[57] ABSTRACT

An analytical process for enzymatic determination of a substrate in biological fluids. The fluid sample is reacted first in the absence of the specific kinase but in the presence of an NADH — regenerating enzymatic system with the reagents needed for the reaction sequence; then the enzymes are separated from the reaction solution, and thereafter the necessary enzymes are added to the filtrate and NADH consumption is measured.

The method is very accurate, economical in requiring less enzymes and only one measurement is necessary.

13 Claims, No Drawings

ANALYTICAL ENZYMATIC DETERMINATION

The present invention is concerned with an analytical process for the enzymatic determination of substrates in biological fluids, especially in body fluids, such as serum.

In analysis, components in biological fluids are frequently determined according to the following general reaction scheme:

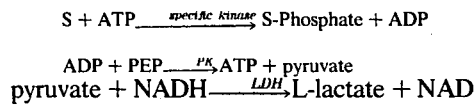

$$ADP + PEP \xrightarrow{PK} ATP + \text{pyruvate}$$
$$\text{pyruvate} + NADH \xrightarrow{LDH} L\text{-lactate} + NAD$$

In the above-given equations, S is the substrate to be determined or a reaction product obtained by a preceding enzymatic reaction, ATP is adenosine triphosphate, S-phosphate is the phosphorylated substrate or reaction product, ADP is adenosine diphosphate, PEP is phosphoenol pyruvate, PK is pyruvate kinase, NADH is reduced nicotinamide-adenine-dinucleotide, LDH is lactate dehydrogenase and NAD is oxidised nicotinamide-adenine-dinucleotide.

In the above-given reaction sequence, the amount of ADP formed in the first reaction is directly proportional to the unknown amount of S. The measured value is the consumption of NADH, which is routinely measured by the determination of the decrease of absorption at 340 nm, Hg 365 or 335. The above-given reaction system is of general utility for the determination of substances which can be phosphorylated, under the influence of a specific kinase, by ATP with the formation of ADP or of substances from which there can be obtained correspondingly phosphorylatable reaction products.

The above-described reaction scheme is used to an especially large extent in the clinical-chemical laboratory for the determination of various substrates, the specificity for a particular substrate being, in each case, achieved by the specific kinase, However, the system suffers from the disadvantage that, in biological fluids, such as body fluids, such as body fluids and especially in serum, other substances are, as a rule, present which also lead to a reaction which consumes NADH. This applies especially to endogenic pyruvate. A further reason for taking into account a blank value is the differing inherent absorption of the biological or body fluids at the mentioned wavelengths, for example, because of its bilirubin content. Therefore, as a rule, such determinations are carried out together with a sample blank value in which the specific kinase, i.e. the phosphorylating enzyme, is absent. By subtration of the results obtained in the two parallel determinations, the content of the desired substance can then be determined. It is disadvantageous that twice as much of the very expensive enzymatic reagents are required as would have been necessary for a determination involving only one measurement so that the cost of the reagents is practically doubled. It is also disadvantageous that the process can only be carried out with the automatic analysis apparatus at present in use when two measurement channels are available.

Another possibility for removing errors caused by endogenic substances is to allow the endogenic substances to be used up by a reaction taking place before the addition of the specific kinase, in a first determination to measure the consumption of NADH, then to add the specific kinase and again to measure the NADH consumption. This process is laborious and suffers from the especially severe disadvantage that it cannot be carried out at all in known automatic analysis devices.

It is, therefore, an object of the present invention to provide a process of the above-described type in which it is only necessary to carry out a single measurement and in which the consumption of enzymes is reduced. A further object of the present invention is to provide a process which can also be carried out in conventional automatic analysis devices.

Thus, according to the present invention, there is provided an analytical process for the enzymatic determination of substrates in biological fluids, especially in serum, by the phosphorylation of a substrate or of a reaction product enzymatically obtained from a substrate, with ATP in the presence of a specific kinase, with the liberation of ADP, reaction of the latter with phosphenol pyruvate in the presence of pyruvate kinase, with the formation of pyruvate, hydrogenation of the pyruvate by means of NADH in the presence of lactate dehydrogenase and measurement of the NADH consumption, wherein the fluid sample is reacted in the absence of the specific kinase and in the presence of an NADH-regenerating enzymatic system with the reagents needed for the reaction sequence, whereafter the enzymes are separated off from the reaction solution, for example by a semi-permeable membrane or by centrifuging, the specific kinase, pyruvate kinase and lactate dehydrogenase are added to the filtrate and the measurement is carried out.

The process according to the present invention can, in principle, be used for all enzymatic analytical processes in which either the substrate to be determined itself or also the product of a preceding enzymatic reaction is reacted with ATP. Examples of such processes include the determination of free glycerol (Klin. Wschr., 40. 362/1962), of neutral fat (Klin. Wschr., 44, 262/1966), of creatinine (Scand. J. Clin. Lab. Invest., 29, Suppl., 126/1972) and of glucose (Biochem. Z., 328, 499/1957).

If the substrate of the specific kinase is itself determined, for example, in the case of the measurement of free glycerol, then only the kinase specific for this is added, i.e. in this particular case, glycerol kinase. If the kinase phosphorylates a reaction product obtained enzymatically from the actual substance to be determined, then, in addition, there is also needed the enzymatic reaction system for obtaining the reaction product from the substrate in a first process step.

An example of this is the determination of neutral fat (triglyceride determination), in which the fats are reacted with lipase and possibly with esterase, with the formation of glycerol and fatty acid, whereafter the glycerol formed is phosphorylated with ATP and glycerol formed is phosphorylated with ATP and glycerol kinase.

The reagents needed for the reaction sequence are, apart from the mentioned enzymes, ATP, PEP and NADH, also adjuvants, such as buffer substances, inorganic salts, for example magnesium sulphate, and possibly also surface-active substances and the like. All these materials are well known for the reaction sequence in question to be carried out and do not need to be described here in detail.

The NADH-regenerating enzymatic system consists essentially of an NADH-specific dehydrogenase, as well as a substrate for this dehydrogenase for example the enzymatic system consisting of Glucose-6-phosphate (G-6-P) and Glucose-6-phosphate-dehydrogenase (G6P-DH) from Leuconostoc mesenteroides. This system regenerates NADH from NAD according to the following reaction:

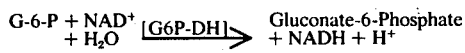

$$\text{G-6-P} + \text{NAD}^+ + \text{H}_2\text{O} \xrightarrow{[\text{G6P-DH}]} \text{Gluconate-6-Phosphate} + \text{NADH} + \text{H}^+$$

According to the present invention, a preferred system of this type contains alcohol dehydrogenase and, as substrate, alcohol. Other NADH-specific dehydrogenases and substrates for them can however, be used in the same way. The process of the invention is of general applicability in the determination of substances which can be phosphorylated in the presence of ATP and ADP, as the carrier system in the presence of a specific kinase, a "phosphokinase" which catalyzes the transfer of the phosphate radical. Some technical substrates with the reactants involved are illustrated below, ATP and ADP being present too.

| SUBSTANCE | PRODUCT | ENZYMES |
|---|---|---|
| Creatine | creatine phosphate | "Lohmann enzyme" |
| Arginine | arginine phosphate | Arginine phosphokinase |
| Glucose | glucose-6-phosphate | Hexokinase |
| Fructose | fructose-6-phosphate | Fructosehexokinase |
| Mannose | mannose-6-phosphate | Mannohexokinase |
| Galactose | galactose-1-phosphate | Galactohexokinase |
| Fructose-6-phosphate | fructose-1:6-diphosphate | Phosphohexokinase |
| 3-Phosphoglyceric acid | 1:3-diphosphoglyceric | Phosphoglyceric phosphokinase |
| Adenosine monophosphate | adenosine diphosphate | Myokinase |
| Adenosine | adenosine monophosphate | Adenosinekinase |
| Riboflavin | riboflavin phosphate | Flavokinase |

As semi-permeable membrane, according to the present invention, there is used a membrane which is impermeable selectively for proteins but is permeable to low molecular weight substances. Examples of membranes of this type include dialysis membranes, ultrafiltration membranes, membranes for reverse osmosis and the like. Instead of using a semi-permeable membrane, the separation can, as mentioned above, also be carried out by centrifuging, or other suitable method.

In carrying out the process according to the present invention in a commercially available automatic analysis device, as semi-permeable membrane for the separation of the proteins, there can be used the dialysis apparatus which is, as a rule, provided in such apparatus. It is, therefore, possible to carry out the process according to the present invention on such automatic apparatus without having to alter it and without a second measurement channel being necessary. In the case of this embodiment of the present invention, use is, therefore, in principle made of a compartimentalization or segregation of the reactions, whereby the enzymatic reactions, with the exception of the phosphorylation with ATP (because of the absence of the specific kinase), takes place in the first compartment, the low molecular weight components then pass through a semi-permeable membrane into a second compartment, without any measurement being necessary, the specific kinase, PK and LDH then are added to the filtrate in the second compartment, and then the NADH consumption is measured photometrically. Since, due to the action of the semi-permeable membrane, the NADH-regenerating system is also excluded because of the separation of the dehydrogenase needed therefor, the measured NADH consumption corresponds solely to the amount of the phosphorylated substances, with the exclusion of side reactions. The extent of the side reactions thus avoided can be measured when, for example in the case of serum, the there conventional pyruvate concentrations are compared with the concentrations which various substances to be determined in the serum normally exhibit according to the above-described process:

| substrate component | concentration normal range (mM) | % content of the pyruvate, referred to substrate |
|---|---|---|
| pyruvate | 0.05 – 0.07 | — |
| triglyceride | 0.8 – 1.94 | 3 – 10% |
| free glycerol | 0.03 – 0.145 | 30 – 200% |
| creatinine | 0.07 – 0.13 | 40 – 100% |

The above Table shows that merely the error in measurement to the pyruvate can account for a multiple of the measurement value due to the substrate. It is also to be added that, in many cases, biological fluids can also contain other disturbing materials, such as bilirubin, the influence of which is also excluded by the process according to the present invention. In order to demonstrate this, increasing amounts of bilirubin (up to 10 mg./100 ml.) were dissolved in a serum. The determination of the glycerol content with such a reagent mixture gave the same values with and without bilirubin. With the omission of the NADH-regenerating system, there were obtained about 10% higher measurement values which depend upon the endogenic pyruvate content but, surprisingly, were practically independent of the bilirubin concentration. Therefore, by means of the process according to the present invention, disturbances are also excluded which are attributable to an inherent coloration of the biological fluid. The reason for this effect is not known.

Since it is not necessary to determine a blank value, the consumption of expensive enzymes is halved and, at the same time, the use of the process in automatic analysis devices is not only retained but it is also possible to use those automatic analysis devices which only have a single measurement. In the case of automatic analysis devices with two measurement, not only is one measurement kept free for another determination but operating also becomes much simpler since the chronological, electronic and optical adjustment of two automatic analysis device is saved.

According to the present invention, disturbances due to a content of high molecular weight proteins, which strongly scatter light and, in this way, simulate a light absorption, for example in the case of strongly lipaemic sera, are excluded.

Especially good results are obtained with the process according to the present invention using ethanol and alcohol dehydrogenase (ADH) as the NADH-regenerating system when the ethanol concentration is at least 2 g./100 ml. buffer and the ADH concentration is at least 180 IU/ml. In this case, triethanolamine buffer (0.05 to 0.2M) with a pH of 7 to 8, is especially useful.

The following Examples are given for the purpose of illustrating the present invention:

EXAMPLE 1

Glycerol determination

For the determination, there was used an aqueous sample with a glycerol concentration of 30 mg./100 ml. The influence of pyruvate was studied by the addition of 2, 4, 6, 8 and 10 mg. pyruvate to 100 ml. of sample. The determination was carried out on an AutoAnalyser, IInd generation, which is an automatic analysis apparatus of the firm Technicon, U.S.A.. This apparatus operates with a continuous flow system, the dosings of the individual reagents being given therefore in the dimension (ml./min.). For the separation of the enzymes, there was used a commercially available dialysis cell of the firm Technicon, U.S.A.

The sample (0.05 ml./min.) was diluted with a solution, at a rate of flow of 0.8 ml./min., containing triethanolamine buffer (0.1M; pH = 7.6), NADH (0.025 mM), ATP (0.13mM), PEP (0.04 mM), magnesium sulphate (1.0 mM), ethanol (2 g./100 ml.) and the enzymes LDH (1.6 IU/ml.), PK (0.3 IU/ml.), as well as ADH (180 IU/ml.). Dialysis is carried out against a solution containing triethanolamine buffer (0.1M; pH 7.6), with NADH (0.1 mM), ATP (0.53 mM), PEP (0.18 mM), magnesium sulphate (1.0 mM), LDH (6.4 IU/ml.), PK (1 IU/ml.), with a rate of flow of 0.6 ml./min.

The dialysate is mixed with a solution of glycerokinase (2 IU/ml. in 7.5 mM magnesium sulphate) at a rate of flow of 0.1 ml./min. The decrease of extinction, expressed as scale parts, is measured after an incubation of 7.5 minutes at 37° C. The results obtained are set out in the following Table 1:

TABLE 1

| Sample | Added pyruvate mg./100 ml. | Findings Column 1 with serum blank | | Column 2 without serum blank and without NADH-regenerating system | | Column 3 according to the invention | |
|---|---|---|---|---|---|---|---|
| | | Scale parts | % finding | Scale parts | % finding | Scale parts | % finding |
| 1 | — | 72 | 100 | 73 | 101 | 71.5 | 99. |
| 2 | 2 | 72 | 100 | 78 | 108 | 72 | 100 |
| 3 | 4 | 74 | 102.7 | 81.5 | 113 | 72.5 | 100.6 |
| 4 | 6 | 72.5 | 100.6 | 86 | 119 | 72.5 | 100.6 |
| 5 | 8 | 73 | 101 | 91.5 | 127 | 72 | 100 |
| 6 | 10 | 72 | 100 | 96.5 | 134 | 71 | 98.5 |

Sample 1 contains 30.0 mg. glycerol in 100 ml. double distilled water.

It can clearly be seen that only the process according to the present invention (column 3) using one measurement channel provides values agreeing with the values adjudged to be correct using the 2-channel process with sample blank value (column 1).

EXAMPLE 2

Determination of neutral fat in human serum

As samples, human serum were taken to which pyruvate was added in concentrations of 2, 4, 6, 8 and 10 mg./100 ml. The apparatus used was the same as that described in Example 1. The solutions contained the following components and were pumped at the given rates of flow

Solution 1

0.1M triethanolamine buffer (ph 7.8) at 0.8 ml./min., containing 0.025 mM NADH, 0.13 mM ATP, 0.04 mM PEP, 1.0 mM magnesium sulphate, 2 g./100 ml. ethanol, 1.6 IU LDH/ml., 0.26 IU PK/ml., 180 IU ADH/ml., 11 IU esterase/ml., 400 IU lipase/ml. and 0.1 mg. sodium dodecyl sulphate/ml.

Solution 2 (dialysate)

0.1M triethanolamine buffer (pH 7.6 at 0.6 ml./min., containing 0.1 mM NADH, 0.53 mM ATP, 0.18 mM PEP, 1.0 mM magnesium sulphate, 6.4 IU LDH/ml. and 1.0 IU PK/ml.

Solution 3

7.5 mM magnesium sulphate at 0.1 ml./min., containing 2 IU glycerokinase/ml.

The incubation period at 37° C is 7.5 minutes.

The measurement values obtained are set out in the following Table 2:

TABLE 2

| Sample | added pyruvate mg./100 ml. | Findings Column 1 with serum blank | | Column 2 without serum blank and without NADH-regenerating system | | Column 3 according to the invention | |
|---|---|---|---|---|---|---|---|
| | | Scale parts | % finding | Scale parts | % finding | Scale parts | % finding |
| Sample 1 | — | 29 | 100 | 31 | 106.8 | 29 | 100 |
| = 138 mg. | 2 | 29 | 100 | 35.5 | 122 | 29 | 100 |
| neutral | 4 | 29 | 100 | 39.5 | 136 | 29.5 | 102 |
| fat/100 ml. | | | | | | | |
| serum | 6 | 28 | 97 | 44.5 | 153 | 29.0 | 100 |
| | 8 | 28 | 97 | 49 | 168 | 29.0 | 100 |

TABLE 2-continued

| Sample | added pyruvate mg./100 ml. | Findings | | | | | |
|---|---|---|---|---|---|---|---|
| | | Column 1 with serum blank | | Column 2 without serum blank and without NADH-regenerating system | | Column 3 according to the invention | |
| | | Scale parts | % finding | Scale parts | % finding | Scale parts | % finding |
| | 10 | 28 | 97 | 53.5 | 184 | 29.0 | 100 |
| Sample 2 = 114 mg. neutral fat/100 ml. serum | — | | | 21.5 | 113 | 19 | 100 |
| | 2 | | | 25 | 131 | 19 | 100 |
| | 4 | | | 28.5 | 150 | 19 | 100 |
| | 6 | | | 32 | 168 | 19 | 100 |
| | 8 | | | 36.5 | 192 | 19 | 100 |
| | 10 | | | 40.5 | 213 | 19 | 100 |

EXAMPLE 3

Exclusion of interferences of other coloured substances

A sample in which neutral fat is to be determined is mixed with a sample which contains a high concentration of bilirubin. (Bilirubin is a decomposition product, natural to the body, of blood colouring material which, at 340 or 366 nm, shows an absorption limit; the maximum lies at 450 nm). Otherwise, the experiment conditions maintained were the same as those used in Example 2, with the exception that, for a control in the experimental series, column 3 was measured without the kinase (glycero-kinase). The results obtained are shown in the following Table 3:

TABLE 3

| Sample | Added bilirubin (mg./100 ml.) | Findings | | | | | |
|---|---|---|---|---|---|---|---|
| | | Column 1 without serum blank and with NADH-regenerating system (complete) | | Column 2 without serum blank and without kinase (GK) and NADH-regen. system | | Column 3 according to the invention but without kinase (GK) | |
| | | Scale parts | % finding | Scale parts | % finding | Scale parts | % finding |
| 1 | 0 | 11 | 100 | *) | 9 | 0 | 0 |
| 2 | 0 | 18 | 100 | 1.7*) | 9.5 | 0 | 0 |
| 2 | 2 | 18 | 100 | 1.7*) | 9.5 | 0 | 0 |
| 2 | 5 | 18.5 | 102.7 | 1.7*) | 9.5 | 0 | 0 |
| 2 | 10 | 17.5 | 97.2 | 1.7*) | 9.5 | 0 | 0 |
| 3 | 0 | 37.5 | 100 | 1.3*) | 3.5 | 0 | 0 |

*) This value represents endogenic pyruvate
The finding value of 0% in Column 3 shows that no influence due to bilirubin is measured.

For further disclosure of conventional enzymatic reaction reference may be made to Dynamic Aspects of Biochemistry Baldwin, 2d Ed., 1952, Cambridge University Press.

What we claim is:

1. In an analytical process for enzymatic determination of a substrate in a biological fluid by phosphorylation of a substrate with ATP with the liberation of ADP, reaction of ADP with phosphoenol pyruvate in the presence of pyruvate kinase with the formation of pyruvate, hydrogenation of the pyruvate with NADH in the presence of lactate dehydrogenase, the improvement which comprises,
    reacting the biological fluid substrate, in the absence of its specific kinase but in the presence of a NADH-regenerating enzymatic system which is the specific dehydrogenase and a substrate for the dehydrogenase with adenoisine triphosphate, phosphoenol pyruvate, and NADH,
    separating the enzymes from the reaction mixture,
    adding the specific kinase for the substrate, pyruvic kinase and lactate dehydrogenase to the liquid product free of enzymes,
    measuring the NADH consumption, thereby measuring only the amount of phosphorylated substrate.

2. The process of claim 1 wherein the NADH-specific dehydrogenase is alcohol dehydrogenase, and a substrate therefor.

3. The method of claim 2 wherein the substrate is an alcohol.

4. The process of claim 3 wherein the alcohol is ethanol.

5. The process of claim 1 wherein the substrate is glycerol and the specific kinase added to the liquid product free of enzymes is glycerol kinase.

6. The process of claim 1 wherein the substrate is the reaction product of a prior enzymatic reaction.

7. The process of claim 6 wherein the substrate is glycerol and a fatty acid, which are enzymatically obtained using lipase.

8. The process of claim 7 wherein the substrate is obtained using also esterase.

9. The process of claim 8 wherein glycerol is formed and the specific kinase is glycerol kinase.

10. The process of claim 1 wherein the separation is by dialysis.

11. The process of claim 1 wherein the separation of the enzymes is carried out by means of a semi-permeable membrane selective for low molecular weight substances which prevents the passage of enzymes.

12. The process of claim 1 wherein the biological fluid containing the substrate also contains dissolved bilirubin through the series of reactions, which bilirubin is separated from the reaction mixture.

13. The process of claim 1 wherein the substrate is a triglyceride.

* * * * *